US007537757B2

(12) United States Patent
Schwarz

(10) Patent No.: US 7,537,757 B2

(45) Date of Patent: May 26, 2009

(54) METHODS OF FACILITATING VASCULAR GROWTH IN CARDIAC MUSCLE AND METHODS FOR THE PRODUCTION OF RECOMBINANT EMAP II

(75) Inventor: Margaret A. Schwarz, La Canada-Flintridge, CA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 251 days.

(21) Appl. No.: 09/733,306

(22) Filed: Dec. 8, 2000

(65) Prior Publication Data

US 2001/0041680 A1 Nov. 15, 2001

Related U.S. Application Data

(60) Provisional application No. 60/241,138, filed on Oct. 17, 2000, provisional application No. 60/231,759, filed on Sep. 12, 2000, provisional application No. 60/197,558, filed on Apr. 17, 2000, provisional application No. 60/171,874, filed on Dec. 23, 1999.

(51) Int. Cl.
*A61K 39/395* (2006.01)
*A61K 38/04* (2006.01)
*C07K 16/18* (2006.01)

(52) U.S. Cl. .............. 424/130.1; 424/133.1; 424/141.1; 424/145.1; 530/327; 530/387.1; 530/387.3; 530/388.15; 530/388.24

(58) Field of Classification Search ..................... 514/2, 514/44; 435/6, 325, 366; 530/387.1, 350, 530/300
See application file for complete search history.

(56) References Cited

U.S. PATENT DOCUMENTS 5,641,867 A * 6/1997 Stern et al. ............. 530/388.23
6,017,898 A 1/2000 Pietrzkowski et al.
6,174,906 B1 1/2001 Elliott et al.
6,306,612 B1 * 10/2001 Schwarz et al. .............. 435/7.1
6,914,128 B1 * 7/2005 Salfeld et al. ............ 530/387.3
2003/0215421 A1 * 11/2003 McDonald et al. ......... 424/85.1

OTHER PUBLICATIONS

Meyerson et al. Journal of Cardiovascular Nursing. 1999. vol. 13(4), pp. 91-109.*

Stryer et al. in Biochemistry, Third edition, W.H. Freeman Company, New York, pp. 31-33, 1998.*

Thompson et al. (2004) Journal of Surgical Research, vol. 116, pp. 156-164.*

Murray et al. (2000), American Journal of Pathology, Vo. 157, No. 6, pp. 2045-2053.*

Schwarz et al. Am J Physiol. Feb. 1999;276(2 Pt 1):L365-75.*

Kuby et al, Immunology, Second edition, pp. 86-96, 1994.*

Flanagan et al, Cellular penetration and antisense activity by a phenoxazine-substituted heptanucleotide, Nat Biotechol 17(1): 48-52, Jan. 1999.*

Branch et al, A good antisense molecule is hard to find, Trends BIochem Sci 23(2): 45-50, Feb. 1998.*

Schluesener HJ et al. Localization of endothelial-monocyte-activating polypeptide II (EMAP II), a novel proinflammatory cytokine, to lesions of experimental autoimmune encephalomyelitis, neuritis and uveitis: expression by monocytes and activated microglial cells. Glia. (1997) 20:365-372.

Knies UE et al. Regulation of endothelial monocyte-activating polypeptide II release by apoptosis. Proc. Natl. Acad. Sci. USA. (Oct. 1998) 95:12322-12327.

Schwarz MA et al. Angiogenesis and morphogenesis of murine fetal distal lung in an allograft model. Am J Physiol Lung Cell Mol Physiol. (2000) 278:L1000-L1007.

Zhang F and Schwarz MA. Temporo-spatial distribution of endothelial-monocyte activating polypeptide II, an anti-angiogenic protein, in the mouse embryo. Developmental Dynamics. (2000) 218:490-498.

Zhu Z et al. Clinical development of angiogenesis inhibitors to vascular endothelial growth factor and its receptors as cancer therapeutics. (2002) 2(2):135-156.

Murray JC et al. Endothelial monocyte-activating polypeptide-II (EMAP-II): a novel inducer of lymphocyte apoptosis. Journal of Leukocyte Biology. (May 2004) 75:772-776.

Quintos-Alagheband ML et al. Potential role for antiangiogenic proteins in the evolution of bronchopulmonary dysplasia. Antioxidant & Redox Signaling. (Nov. 1, 2004) 6(1):137-145.

Schwarz MA et al. Epithelial-mesenchymal interactions are linked to neovascularization. Am. J. respire. Cell Mol. Biol. (2004) 30:784-792.

Zohlnhöfer D et al. Rapamycin effects transcriptional programs in smooth muscle cells controlling proliferative and inflammatory properties. Molecular Pharmacology. (2004) 65(4):880-889.

(Continued)

*Primary Examiner*—Phuong Huynh
(74) *Attorney, Agent, or Firm*—Myers Bigel Sibley & Sajovec, PA

(57) ABSTRACT

A method of facilitating vascular growth in cardiac muscle of a subject in need of such treatment comprises inhibiting EMAP II activity in said subject by an amount effective to stimulate vascular growth in said cardiac muscle. The inhibiting step may be carried out by any suitable means, such as: By administering a compound (e.g., an antibody) that specifically binds to EMAP II to said subject in an amount effective to stimulate vascular growth in said cardiac muscle; by down-regulating EMAP II expression in said subject by an amount effective to stimulate vascular growth in said cardiac muscle (e.g., by administration of an antisense olgionucleotide); or by administering an EMAP II receptor antagonist to said subject in an amount effective to stimulate vascular growth in said cardiac muscle.

6 Claims, No Drawings

OTHER PUBLICATIONS

Nührenberg TG et al. EMAP-II downregulation contributes to the beneficial effects of rapamycin after vascular injury. Cardiovascular Research. (2008) 77:580-589.

Kao, Janet, et al., Characterization of a Novel Tumor-derived Cytokine—Endothelial-Monocyte Activating Polypeptide II, *The Journal of Biological Chemistry*, vol. 269, No. 40, pp. 25106-25119, Oct. 7, 1994.

Schwarz, Margaret A., et al., Endothelial-Monocyte Activating Polypeptide II, A Novel Antitumor Cytokine that suppresses Primary and Metastatic Tumor Growth and Induces Apoptosis in Growing Endothelial Cells, *J. Exp. Med.*, vol. 190, No. 3, pp. 341-353, Aug. 2, 1999.

Kao, Janet, et al., *Endothelial Monocyte-activating Polypeptide II—A Novel Tumor-Derived Polypeptide that Activates Host-Response Mechanisms*, The J. of Biological Chemistry, vol. 267, No. 28, pp. 20239-20247, Oct. 5, 1992.

* cited by examiner

METHODS OF FACILITATING VASCULAR GROWTH IN CARDIAC MUSCLE AND METHODS FOR THE PRODUCTION OF RECOMBINANT EMAP II

RELATED APPLICATIONS

This application claims the benefit of U.S. Provisional Application Ser. No. 60/171,874, filed Dec. 23, 1999, of U.S. Provisional Application Ser. No. 60/197,558, filed Apr. 17, 2000, of U.S. Provisional Application Ser. No. 60/231,759, filed Sep. 12, 2000, and of U.S. Provisional Application Ser. No. 60/241,138, filed Oct. 17, 2000, the disclosures of all of which are incorporated by reference herein in their entirety.

STATEMENT OF FEDERAL SUPPORT

This invention was made with Government support under Grant Numbers NIH HL-60061. The Government has certain rights to this invention.

FIELD OF THE INVENTION

The present invention concerns methods of facilitating vascular growth in cardiac muscle in a subject in need of such treatment, including subjects afflicted with myocardial ischemia, atherosclerosis, and other myocardial disease such as cardiomyopathy or cardiac hypertrophy.

BACKGROUND OF THE INVENTION

Cardiovascular disease is the leading cause of morbidity and mortality in the United States, causing forty-one percent of all deaths. Following coronary artery occlusion, myocardial recovery is dependent on the heart's ability to develop collateral circulation and revascularize the infarcted myocardium. Although much is known about positive growth factors such as vascular endothelial growth factor (VEGF) and basic fibroblast growth factor (bFGF) that promote myocardial revascularization following myocardial infarction, the molecular mechanisms opposing these stimuli are unknown (see, e.g., J. Li et al., VEGF, flk-1, and flt-1 expression in a rat myocardial infarction model of angiogenesis, *Am J Physiol.* 270: H1803-11 (1996); K. Shinohara et al., Expression of vascular endothelial growth factor in human myocardial infarction, *Heart Vessels* 11 113-22 (1996); M. Miyataka et al., Basic fibroblast growth factor increased regional myocardial blood flow and limited infarct size of acutely infarcted myocardium in dogs, *Angiology* 49, 381-90 (1998); M. Horrigan et al., Reduction in myocardial infarct size by basic fibroblast growth factor following coronary occlusion in a canine model, *Int J Cardiol.* 10, S85-91 (1999); D. Losordo et al., Gene therapy for myocardial angiogenesis: initial clinical results with direct myocardial injection of phVEGF165 as sole therapy for myocardial ischemia, *Circulation* 98, 2800-4 (1998); and U.S. Pat. No. B1 5,661,144 to Leiden et al., (Reexamination Certificate Issued Jun. 1, 1999)). Accordingly, there is a need for new ways to treat cardiovascular disease.

SUMMARY OF THE INVENTION

A first aspect of the present invention is a method of facilitating vascular growth in cardiac muscle of a subject in need of such treatment. The method comprises inhibiting EMAP II activity in said subject by an amount effective to stimulate vascular growth in said cardiac muscle. The inhibiting step may be carried out by any suitable means, such as: by administering a compound that specifically binds to EMAP II to said subject in an amount effective to stimulate vascular growth in said cardiac muscle; by downregulating EMAP II expression in said subject by an amount effective to stimulate vascular growth in said cardiac muscle; or by administering an EMAP II receptor antagonist to said subject in an amount effective to stimulate vascular growth in said cardiac muscle.

Stated otherwise, the present invention provides a method of facilitating vascular growth in cardiac muscle tissue of a subject in need of such treatment, the method comprising administering to the subject an active agent that inhibits EMAP II activity in said subject by an amount effective to promote blood vessel formation in the cardiac muscle. Any suitable active agent may be employed, including: a compound that specifically binds to EMAP II (e.g., an antibody); a compound that downregulates EMAP II expression (e.g., an antisense oligonucleotide); or an EMAP II receptor antagonist.

A further aspect of the present invention is a method of making recombinant EMAP II, comprising the steps of: providing a cell lysate, said cell lysate comprising recombinant EMAP II; passing said cell lysate through a nickel column under conditions in which said recombinant EMAP II is bound to said nickel column; and then eluting said recombinant EMAP II from said nickel column.

A still further aspect of the present invention composition comprising isolated recombinant EMAP II having a shelf life of at least 6 months or 1 year under frozen conditions. The composition may optionally be provided in sterile form.

A still further aspect of the present invention is a pharmaceutical formulation comprising isolated recombinant EMAP II according in a sterile pharmaceutically acceptable carrier, and having a shelf life of at least 6 months or 1 year under frozen conditions.

A further aspect of the present invention is the use of an active agent as described above for the preparation of a medicament for carrying out the methods described above.

The present invention is explained in greater detail in the specification set forth below.

DETAILED DESCRIPTION OF PREFERRED EMBODIMENTS

As noted above, a first aspect of the invention is a method of facilitating vascular growth in a muscle, particularly cardiac muscle, of a subject in need of such treatment. The method comprises inhibiting EMAP II activity in the cardiac muscle of the subject by an amount effective to stimulate vascular growth therein.

By "facilitating" vascular growth is meant any enhancement, improvement in, stimulation of, promotion of or increase in vascular growth, without reference to any particular underlying mechanism thereof.

Applicant's invention is not intended to be limited to any particular theory of vascular growth, and hence this term is intended to be construed generally, encompassing any type of vascular growth such as vasculogenesis, angiogenesis, etc.

While subjects treated by the present invention are primarily human subjects, the invention may also be carried out on other animal subjects such as dogs, cats, horses, etc. for veterinary purposes.

1. Methods of Treatment.

The present invention may be employed for any subject in need of a treatment as described herein, including but not limited to subjects afflicted with myocardial ischemia, atherosclerosis, and other myocardial disease such as cardiomyopathy or cardiac hypertrophy.

The inhibiting step may be carried out by any suitable means. For example, it may be carried out by administering a compound that specifically binds to EMAP II to the subject in an amount effective to stimulate vascular growth. Such compounds may be antibodies (including polyclonal and monoclonal antibodies, antibody fragments, humanized or chimeric antibodies, etc. that retain the combining region that specifically binds to EMAP II). The antibodies may be of any type of immunoglobulin, including but not limited to IgG and IgM immunoglobulins. The antibodies may be of any suitable origin, such as chicken, goat, rabbit, horse, etc., but are preferably mammalian and most preferably human. The antibody may be administered directly or through an intermediate that expresses the antibody in the subject. Examples of EMAP II antibodies are provided in U.S. Pat. No. 5,641,867 to Stern et al., the disclosure of which is incorporated herein by reference. Examples of the different forms of therapeutic antibodies are given in U.S. Pat. No. 5,622,700, the disclosure of which is incorporated herein by reference.

The inhibiting step may be carried out by downregulating EMAP II expression in the subject by an amount effective to stimulate vascular growth in the lungs of the subject. Compounds useful for downregulating EMAP II expression are, in general, antisense oligonucleotides that bind to EMAP II mRNA and disrupt translation thereof, or oligonucleotides that bind to EMAP II DNA and disrupt transcription thereof. Such oligonucleotides may be natural or synthetic (such as described in U.S. Pat. No. 5,665,593 to Kole, the disclosure of which is incorporated by reference herein in its entirety), and are typically at least 4, 6 or 8 nucleotides in length, up to the full length of the corresponding DNA or mRNA. Such oligonucleotides are selected to bind to the DNA or mRNA by Watson-Crick pairing based on the known sequence of the EMAP II DNA as described in U.S. Pat. No. 5,641,867 to Stern et al., the disclosure of which is incorporated by reference herein in its entirety. For example, an antisense oligonucleotide of the invention may consist of a 4, 6 or 8 or more nucleotide oligonucleotide having a base sequence corresponding to the EMAP II DNA sequence (SEQ ID NO:2) disclosed in Stern et al., supra, up to 20, 30, or 40 nucleotides in length, or even the full length of the mRNA/DNA sequence coding for EMAP II (SEQ ID NOS:3 and 4) disclosed in Stern et al., supra. In addition, such compounds may be identified in accordance with known techniques as described below.

The inhibiting step may be carried out by administering an EMAP II receptor antagonist to the subject in an amount effective to stimulate vascular growth in the lungs of the subject. EMAP II receptor antagonists may be identified in accordance with known techniques, but are in general analogs of EMAP II, such as EMAP II having three to five N-terminal and/or C-terminal amino acids deleted.

Active compounds useful for effecting the aforesaid inhibiting steps may be administered by any suitable means, including intraperitoneal, subcutaneous, intraarterial, intravenous, and intramuscular injection (including into cardiac muscle). Injection may be through a syringe, through a canula or catheter into a desired vessel or region of the heart, etc. Injection may be into the myocardium of the subject, such as by direct injection into a ventricular wall of the heart of an afflicted subject.

Pharmaceutical formulations of the invention typically comprise an active compound selected from the group consisting of compounds that specifically bind to EMAP II (e.g., an antibody as described above), compounds that inhibit the expression of EMAP II, and EMAP II receptor antagonists; and a pharmaceutically acceptable carrier. Any pharmaceutically acceptable carrier may be employed, such as sterile saline solution, sterile water, etc. The active compound is included in the pharmaceutically acceptable carrier in any suitable amount, such as between about 0.001, 0.005 or 0.01 percent by weight to about 10, 20, 50 or 90 percent by weight by weight, or more.

Dosage of the active compound will depend upon the particular active compound, the route of administration, the particular disorder being treated, the age, weight, and condition of the subject, etc. For example, for antisense oligonucleotides, the dosage is preferably one which produces intracellular concentrations of the oligonucleotide of from 0.05 to 50 μM. Typically the dosage to a human will be from about 0.01, 0.1 or 1 mg/Kg up to 50, 100, or 150 mg/Kg. In an additional example, for antibodies, the dosage is typically 0.01, 0.05 or 0.1 up to 20, 40 or 60 mg/Kg.

Active compounds that are nucleotides or proteins (e.g., antibodies) may be administered either directly as described above or through a vector intermediate that expresses the same in the subject. Thus vectors used to carry out the present invention are, in general, RNA virus or DNA virus vectors, such as lentivirus vectors, papovavirus vectors (e.g., SV40 vectors and polyoma vectors), adenovirus vectors and adeno-associated virus vectors. See generally T. Friedmann, Science 244, 1275 (June 1989). Examples of lentivirus vectors that may be used to carry out the present invention include Moloney Murine Leukemia Virus vectors, such as those described in U.S. Pat. No. 5,707,865 to Kohn. Any adenovirus vector can be used to carry out the present invention. See, e.g., U.S. Pat. No. 5,518,913, U.S. Pat. No. 5,670,488, U.S. Pat. No. 5,589,377; U.S. Pat. No. 5,616,326; U.S. Pat. No. 5,436,146; and U.S. Pat. No. 5,585,362 (the disclosures of all United States patent references cited herein are to be incorporated herein by reference). The adenovirus can be modified to alter or broaden the natural tropism thereof, as described in S. Woo, *Adenovirus redirected*, Nature Biotechnology 14, 1538 (November 1996). Any adeno-associated virus vector (or AAV vector) can also be used to carry out the present invention. See, e.g., U.S. Pat. No. 5,681,731; U.S. Pat. No. 5,677,158; U.S. Pat. No. 5,658,776; U.S. Pat. No. 5,658,776; U.S. Pat. No. 5,622,856; U.S. Pat. No. 5,604,090; U.S. Pat. No. 5,589,377; U.S. Pat. No. 5,587,308; U.S. Pat. No. 5,474,935; U.S. Pat. No. 5,436,146; U.S. Pat. No. 5,354,678; U.S. Pat. No. 5,252,479; U.S. Pat. No. 5,173,414; U.S. Pat. No. 5,139,941; and U.S. Pat. No. 4,797,368. The regulatory sequences, or the transcriptional and translational control sequences, in the vectors can be of any suitable source, so long as they effect expression of the heterologous nucleic acid in the target cells. For example, commonly used promoters are the LacZ promoter, and promoters derived from polyoma, Adenovirus 2, and Simian virus 40 (SV40). See, e.g., U.S. Pat. No. 4,599,308. The heterologous nucleic acid may encode any product that inhibits the expression of the EMAP II gene in cells infected by the vector, such as an antisense oligonucleotide that specifically binds to the EMAP II mRNA to disrupt or inhibit translation thereof, a ribozyme that specifically binds to the EMAP II mRNA to disrupt or inhibit translation thereof, or a triplex nucleic acid that specifically binds to the EMAP II duplex DNA and disrupts or inhibits transcription thereof. All of these may be carried out in accordance with known techniques, as (for example) described in U.S. Pat. Nos. 5,650,316; 5,176,996, or 5,650,316 for triplex compounds, in U.S. Pat. Nos. 5,811,537; 5,801,154; and 5,734,039 for antisense compounds, and in U.S. Pat. Nos. 5,817,635; 5,811,300; 5,773,260; 5,766,942; 5,747,335; and 5,646,020 for ribozymes (the disclosures of which are incorporated by reference herein in their entirety). The length of the heterologous nucleic acid is not critical so long as the intended function is achieved, but the heterologous nucleic acid is typically from 5, 8, 10 or 20 nucleic acids in length up to 20, 30, 40 or 50 nucleic acids in length, up to a length equal the full length of the EMAP II gene. Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques.

The dosage of the recombinant vector administered will depend upon factors such as the particular disorder, the particular vector chosen, the formulation of the vector, the condition of the patient, the route of administration, etc., and can be optimized for specific situations. In general, the dosage is from about $10^7$, $10^8$, or $10^9$ to about $10^{11}$, $10^{12}$, or $10^{13}$ plaque forming units (pfu).

Active compounds of the present invention may be administered either alone or optionally in conjunction with other compounds useful in the facilitating vascular growth. Examples of such agents, referred to herein as "supplemental compounds," include, but are not limited to, vascular endothelial growth factor (VEGF) and basic fibroblast growth factor (bFGF).

The co-administration of supplemental compounds can be performed before, after, or during the administration of the active compound. The supplemental compounds may optionally be administered concurrently. As used herein, the word "concurrently" means sufficiently close in time to produce a combined effect (that is, concurrently may be simultaneously, or it may be two or more events occurring within a short time period before or after each other). Simultaneous administration may be carried out by mixing the compounds prior to administration, or by administering the compounds at the same point in time but at different anatomic sites or using different routes of administration.

2. Methods of Making Recombinant EMAP II.

Recombinant EMAP II has been difficult to purify and provide in a useful form. In particular, previous preparations of EMAP II have not provided as long a shelf life and as great freeze-thaw stability as would be desired. Accordingly, new methods for the purification of recombinant EMAP II that are simple to carry out, and new purified EMAP II preparations that exhibit good shelf life and freeze-thaw stability, would be quite useful.

The method of preparing recombinant EMAP II as described herein involves, first, preparing a cell lysate comprising or containing recombinant EMAP II. The recombinant EMAP II may be include a His-Tag (that is, a polyhistidine segment consisting of at least 6 histidine residues, which may be coupled to the N-terminus of the EMAP II in accordance with known techniques. In a preferred embodiment, EMAP II is placed in a PET 28 vector that adds the 6xHis-tag to the EMAP II protein. Materials may be purchased as the QIAexpressionist™ system available from Qiagen.

The cell lysate can be prepared from any suitable cells that contain a recombinant nucleic acid encoding EMAP II and express the recombinant EMAP II. The EMAP II may include a His-Tag as described above. Suitable cells include, but are not limited to, yeast cells, insect cells, and bacterial cells. Bacterial cells such as *Escherichia coli* cells are currently preferred. The cells may be lysed by any suitable means, including but not limited to sonication and/or the addition of lysozyme to the cell culture medium. For example, the cells may be pelleted by centrifugation and lysed by adding a solution of sodium phosphate, sodium chloride, imidazole and lysozyme to the pellet. Cellular debris is optionally but preferably removed by any suitable means, such as centrifugation or filtration, prior to passing the cell lysate through the nickel column.

Next, the cell lysate is passed through a metal-chelate chromatography column such as a nickel chromatography column so that the recombinant EMAP II binds to the nickel column. Any suitable metal chelate chromatography column can be used.

The recombinant EMAP II may next be eluted from the nickel column by any suitable means, such as by washing the column with an aqueous solution of sodium phosphate, sodium chloride and/or imidazole. The imidazole allows the protein to be isolated in native conditions, coming out of the column already folded by the *E. coli* vector and needing no additional steps for it to be active. The His-Tag segment may optionally be removed from the recombinant EMAP II after elution.

The aqueous wash solution containing the recombinant EMAP II eluted from the nickel column can be further concentrated by dialysis, such as by dialysis three times against a neutral and stable buffer such as phosphate buffered saline. Dialysis is carried out in a manner sufficient to remove substantially or essentially all impurities and endotoxin that may be present.

After dialysis, the recombinant EMAP II may be divided into aliquots and stored for future use under any suitable conditions, such as frozen at −80° C., or lyophilized and stored at −80° C.

All steps prior to freezing or lyophilization, including lysis, passing the lysate through the nickel column, centrifugation, dialysis, etc. are preferably carried out at a temperature of 1, 2 or 3 to 5, 6, 7 or 8° C., and most preferably at 4° C.

The simple procedure described above was unexpectedly found to provide an isolated and purified recombinant EMAP II preparation that exhibits long shelf life and good freeze-thaw stability.

Recombinant EMAP II preparations of the present invention preferably exhibit a shelf life of at least 1, 2 or 6 months or at least 1 to 2 years under deep frozen conditions (e.g., −100 to −60° C., preferably −80° C.), a shelf life of at least 1, 2 or 6 months or 1 to 2 years under standard frozen conditions (e.g., −30 to −10° C., and a shelf life of at least 1, 2 or 6 months or even at least 1 to 2 years under refrigerated conditions (e.g., 1, 2 or 3 to 5, 6 or 7° C., most preferably 4° C.). Preferably the compositions will have a shelf life of up to at least 6 months or 1, 2, 3 or 4 years, or more.

The indicated shelf life is considered maintained if the recombinant EMAP II preparation retains 90 or 95% of its biological in an in vitro assay of EMAP II activity. Examples of such assays include J. Kao et al., *J Biol. Chem.* 269, 25106-19 (1994); J. Kao et al., *J. Biol Chem.* 267, 20239-47 (1992); and M. Schwarz et al., *J. Exp. Med.* 190, 341-354 (1999).

Pharmaceutical formulations comprise recombinant EMAP II prepared as described above and preferably provided in sterile, pyrogen free form by any suitable means, such as filtration or ultrafiltration (e.g., by filtration through a 0.2 micron filter). The formulation can be provided in a suitable sterile pharmaceutically acceptable carrier, such as physiological saline solution, phosphate-buffered saline solution, etc. The pharmaceutical formulations typically comprises from 0.1% to 30 or 50% by weight of EMAP II. The pharmaceutical formulations may optionally contain other ingredients, such as stabilizers, buffers, dispersants, etc., as is known in the art. The pharmaceutical formulations preferably exhibit the same shelf life characteristics as described above in connection with the EMAP II compositions. The pharmaceutical formulations may be provided in any suitable form, with injectible formulations currently preferred. The compositions are preferably provided sealed in a sterile container. Where the pharmaceutical formulations are provided in lyophilized form they may be reconstituted with an appropriate sterile injection vehicle, including aqueous vehicles such as sterile pyrogen free physiological saline solution, for administration to a subject.

Recombinant EMAP II and formulations containing the same are useful for a variety of purposes, including, but not limited to, inhibiting angiogenesis, the treatment of cancer, particularly tumors (e.g., by inhibiting angiogenesis in tumors), including all solid tumors and hematologic malignancies and including but not limited to lung cancer, breast cancer, pancreatic cancer, ovarian cancer, testicular cancer) melanoma, glioblastoma, neuroblastoma, hemangioma, prostate cancer liver cancer, colon cancer, gastric cancer, sarcoma, etc.

In addition to the foregoing, it is found that EMAP II will pass through the blood-brain barrier. Accordingly EMAP II, including recombinant EMAP II produced by the techniques described above or EMAP II produced by other techniques, may be administered to a subject in need thereof to treat a brain tumor in said subject. Suitable subjects are human subjects or other mammalian subjects (dogs, cats, horses) for veterinary purposes. Administration may be by any suitable technique, such as by intravenous, intraperitoneal, and intra tumor (intrathecal or steriotactic into the brain tumor) injection). The tumor is, in general, any solid tumor located in the brain, including primary tumors and secondary tumors originating from tumors or malignancies as described above (e.g., lung, breast, pancreatic, ovarian, testicular, liver, colon, and gastric cancers, melanoma, etc.). Particular examples include but are not limited to glioblastomas and neuroblastomas. The dosage may be in any suitable amount depending upon the particular tumor, the condition and weight of the subject, the route of administration, etc., but can be determined by any suitable technique. In general, the dosage may be from 10, 20 or 40 micrograms up to 400, 1000 or 5000 micrograms per kilogram subject body weight. The EMAP II may be prepared for administration in any suitable pharmaceutically acceptable carrier, such as sterile physiological saline solution, in accordance with known techniques and/or may be prepared by the techniques described hereinabove.

The present invention is explained in greater detail in the following non-limiting examples.

EXAMPLE 1

Delivering a Specific Blocking Antibody to EMAP II Following Myocardial Infarction Generates a Marked and Sustained Improvement in Myocardial Function Myocardial function was determined in rats prior to ligation of the left anterior descending artery (LAD). Following ligation of the LAD, rats were randomized to receive either nonspecific rabbit IgG or rabbit EMAP II antibody (500 micrograms in phosphate-buffered saline) by intraperitoneal injection 1 hour post-infarction and every third day for a total of 3 doses. Rats were evaluated for shortening fraction and cardiac output using m-mode and doppler echocardiography (ECHO). Cardiac output was determined by interrogating aortic outflow doppler velocity, and multiplying this by the area of the left ventricular outflow tract (LVOT) and heart rate. Shortening fraction was determined by measuring the internal diameter of the left ventricle (LV) in diastole, subtracting the LV internal diameter in systole, and dividing by the LV internal diameter in diastole. Myocardial function was determined on postoperative days 3, 7, 14, 28, and 42. Data are given in Table 1 below.

A statistically significant improvement in cardiac output that was due to an improvement in stroke volume in those rats receiving EMAP II antibody compared to vehicle was found (*p<0.01). The shortening fraction is improved in the EMAP II antibody group, however it reaches statistical significance only at 28 days postoperatively. This indicates that inhibition of EMAP II's anti-angiogenic effect improves diastolic function and ventricular contractility.

TABLE 1

| Myocardial Function | | Nonspecific IgG(n = 3) | Anti-EMAP II antibody(n = 4) |
|---|---|---|---|
| Shortening fraction | preop | 44.3 ± 2.6 S.D. | 44.45 ± 4.7 S.D. |
| | 3 days | 27 ± 8.3 | 32.5 ± 6.7 |
| | 7 days | 30.4 ± 4.8 | 37.67 ± 5.5 |
| | 14 days | 34.6 ± 5.7 | 40.3 ± 3.3 |
| | 28 days | 28.8 ± 5 | 41.6 ± 1.9* |
| | 42 days | 28.7 ± 5 | 38.65 ± 4.1 |
| Cardiac Output | preop | 0.091 ± 0.024 L/min | 0.100 ± 0.019 L/min |
| | 3 days | 0.056 ± 0.010 | 0.106 ± 0.028* |
| | 7 days | 0.066 ± 0.026 | 0.105 ± 0.018* |
| | 14 days | 0.067 ± 0.015 | 0.116 ± 0.017* |
| | 28 days | 0.077 ± 0.025 | 0.096 ± 0.028 |
| | 42 days | 0.067 ± 0.023 | 0.097 ± 0.015 |
| Heart Rate | preop | 308 ± 21 bpm | 279 ± 77 bpm |
| | 3 days | 306 ± 41 | 338 ± 21 |
| | 7 days | 298 ± 45 | 285 ± 41 |
| | 14 days | 344 ± 44 | 345 ± 41 |
| | 28 days | 272 ± 34 | 232 ± 5 |
| | 42 days | 293 ± 108 | 275 ± 32 |
| Stroke Volume | preop | 0.298 ± 0.099 ml/beat | 0.369 ± 0.079 ml/beat |
| | 3 days | 0.181 ± 0.01 | 0.312 ± 0.08* |
| | 7 days | 0.226 ± 0.067 | 0.370 ± 0.043* |
| | 14 days | 0.193 ± 0.021 | 0.337 ± 0.032* |
| | 28 days | 0.293 ± 0.130 | 0.414 ± 0.129 |
| | 42 days | 0.229 ± 0.008 | 0.351 ± 0.013* |

*p < 0.01

EXAMPLE 2

Generation of an EMAP II Monoclonal Antibody and rEMAP II Protein Purification Synthesis of recombinant (r) EMAP II from *Escherichia coli*. The cDNA of mature human EMAP II was cloned from RT-PCR products of U937 cells' total RNA based on primers obtained from Genebank (accession no. 10119) into a TA vector obtained from Invitrogen. Confirmation of the clones was provided by sequence analysis, after which the cDNA was inserted into PET28a, a 6x his-tag containing plasmid. *E. coli (DE*3) underwent transformation with the EMAP II/PET28a plasmid and were induced with 1-4 mM Isopropyl Beta-D-Thiogalactopyrano side (IPTG). After 3-4 hours of induction, the cells were pelleted, lysed and the EMAP II protein was purified through the use of a Qiagen Nickel-NTA resin column, in accordance with the manufacturer's protocol, with all procedures performed at 4° C. Briefly, pelleted cells were lysed with 50 mM $NaH_2PO_4$ pH 8.0, 300 mM NaCl, and 10 mM imidazole in the presence of 1 mg/ml lysozyme. Following sonication, cellular debris are removed by centrifugation prior to being loaded on the Nickel-NTA resin. Following washing of the column, rEMAP II is eluted off with 8 M urea, 0.1 M $NaH_2PO_4$, and 0.01 M Tris.Cl pH 5.9. Purified rEMAP II is dialyzed at 4° C. against PBS three times prior to being aliquoted and frozen at −80° C. When an aliquot of rEMAP II was thawed, it was used immediately for experiments (it was not refrozen and used in future studies).

Synthesis of antibody. The antibody is generated from the following peptide sequence:

(C)DAFPGEPDKELNP (SEQ ID NO:1) (corresponding to amino acids #254-266 (SEQ ID NO:6) of SEQ ID NO:4) (C) is a cysteine that is assigned for use in the single point, site-directed conjugation procedure described below, and is not part of the original EMAP II antibody.

The peptide is conjugated to KLH (keyhole limpet hemacyanin) by a single point, site-directed conjugation via the terminal cysteine, in accordance with standard techniques.

For generation of the monoclonal antibody, rabbits are injected with 0.5 mg of the peptide-KLH conjugate emulsified in complete Freund's adjuvant, and subsequent injections in incomplete Freund's adjuvant, at three week intervals for a total of three to four injections. Monoclonal antibodies to EMAP II are then generated in accordance with standard techniques.

The foregoing is illustrative of the present invention, and is not to be construed as limiting thereof. The invention is defined by the following claims, with equivalents of the claims to be included therein.

That which is claimed is:

1. A method of improving myocardial function of a subject in need of such treatment, the method comprising administering an antibody that binds to an epitope of Endothelial Monocyte Activating Polypeptide II (EMAP II), wherein the epitope consists of the amino acid sequence of SEQ ID NO:6, in an amount sufficient to inhibit the anti-angiogenic activity of EMAP II in the subject, thereby improving myocardial function in the subject.

2. The method of claim 1, wherein the subject is afflicted with myocardial ischemia.

3. The method of claim 1, wherein the antibody is a polyclonal, monoclonal or humanized antibody.

4. A method of improving myocardial function of a human subject in need of such treatment, the method comprising administering an antibody that binds to an epitope of Endothelial Monocyte Activating Polypeptide II (EMAP II), wherein the epitope consists of the amino acid sequence of SEQ ID NO:6, in an amount sufficient to inhibit the anti-angiogenic activity of EMAP II in the subject, thereby improving myocardial function in the subject.

5. The method of claim 4, wherein the human subject is afflicted with myocardial ischemia.

6. The method of claim 4, wherein the antibody is a polyclonal, monoclonal or humanized antibody.

* * * * *

SEQUENCE LISTING

```
<160> NUMBER OF SEQ ID NOS: 6

<210> SEQ ID NO 1
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1

Cys Asp Ala Phe Pro Gly Glu Pro Asp Lys Glu Leu Asn Pro
1               5                   10


<210> SEQ ID NO 2
<211> LENGTH: 1086
<212> TYPE: DNA
<213> ORGANISM: Mus musculus
<220> FEATURE:
<221> NAME/KEY: CDS
<222> LOCATION: (64)..(993)

<400> SEQUENCE: 2

gaggctgctc aagagctgcg gttgggtcac cgcttcatgt ttctctgccg attctgggga      60

aag atg gca acg aat gat gct gtt ctg aag agg ctg gag cag aag ggt       108
    Met Ala Thr Asn Asp Ala Val Leu Lys Arg Leu Glu Gln Lys Gly
    1               5                   10                  15

gca gag gcg gat cag atc atc gaa tat ctc aag cag cag gtt gct ctt       156
Ala Glu Ala Asp Gln Ile Ile Glu Tyr Leu Lys Gln Gln Val Ala Leu
                20                  25                  30

ctt aag gag aaa gca att ttg cag gca aca atg aga gaa gaa aag aaa       204
Leu Lys Glu Lys Ala Ile Leu Gln Ala Thr Met Arg Glu Glu Lys Lys
            35                  40                  45

ctt cga gtt gaa aat gct aaa ctg aaa aaa gaa ata gaa gag cta aag       252
Leu Arg Val Glu Asn Ala Lys Leu Lys Lys Glu Ile Glu Glu Leu Lys
        50                  55                  60

caa gag ctg att ctg gca gaa att cat aac gga gtg gag caa gtg cgt       300
Gln Glu Leu Ile Leu Ala Glu Ile His Asn Gly Val Glu Gln Val Arg
    65                  70                  75

gtt cga ttg agt act cca ctg cag acg aac tgt act gct tct gaa agt       348
Val Arg Leu Ser Thr Pro Leu Gln Thr Asn Cys Thr Ala Ser Glu Ser
80                  85                  90                  95
```

-continued

```
gtg gtg cag tct cca tca gta gca acc acc gcc tct cct gct aca aaa      396
Val Val Gln Ser Pro Ser Val Ala Thr Thr Ala Ser Pro Ala Thr Lys
                100                 105                 110

gag cag atc aaa gcg gga gaa gaa aag aag gtg aaa gag aag act gaa      444
Glu Gln Ile Lys Ala Gly Glu Glu Lys Lys Val Lys Glu Lys Thr Glu
            115                 120                 125

aag aaa gga gag aaa aag gag aag cag cag tcg gca gca gca agt act      492
Lys Lys Gly Glu Lys Lys Glu Lys Gln Gln Ser Ala Ala Ala Ser Thr
        130                 135                 140

gac tcc aag cct atc gac gca tcg cgt ctg gat ctt cga att ggt tgt      540
Asp Ser Lys Pro Ile Asp Ala Ser Arg Leu Asp Leu Arg Ile Gly Cys
    145                 150                 155

att gtt act gcc aag aag cac cct gat gca gat tca ctg tat gtg gag      588
Ile Val Thr Ala Lys Lys His Pro Asp Ala Asp Ser Leu Tyr Val Glu
160                 165                 170                 175

gaa gta gat gtg gga gaa gca gcc ccg cgc acg gtc gtc agc ggg ctg      636
Glu Val Asp Val Gly Glu Ala Ala Pro Arg Thr Val Val Ser Gly Leu
                180                 185                 190

gtg aat cat gtt cct cta gaa cag atg caa aat cgt atg gtg gtt tta      684
Val Asn His Val Pro Leu Glu Gln Met Gln Asn Arg Met Val Val Leu
            195                 200                 205

ctc tgt aat ctg aag cct gca aag atg cgg gga gtt ctg tct caa gcc      732
Leu Cys Asn Leu Lys Pro Ala Lys Met Arg Gly Val Leu Ser Gln Ala
        210                 215                 220

atg gtg atg tgt gcc agt tca cca gag aaa gtg gag att ctg gcc cct      780
Met Val Met Cys Ala Ser Ser Pro Glu Lys Val Glu Ile Leu Ala Pro
    225                 230                 235

ccc aac ggg tcc gtt cct ggg gac aga att act ttt gat gct ttt cct      828
Pro Asn Gly Ser Val Pro Gly Asp Arg Ile Thr Phe Asp Ala Phe Pro
240                 245                 250                 255

gga gag cct gac aag gag cta aac cct aag aag aag atc tgg gag cag      876
Gly Glu Pro Asp Lys Glu Leu Asn Pro Lys Lys Lys Ile Trp Glu Gln
                260                 265                 270

atc cag cct gac ctg cac acc aat gct gag tgt gtg gcc aca tac aaa      924
Ile Gln Pro Asp Leu His Thr Asn Ala Glu Cys Val Ala Thr Tyr Lys
            275                 280                 285

gga gct ccc ttt gag gtg aag ggg aag gga gtt tgc aga gcc caa acc      972
Gly Ala Pro Phe Glu Val Lys Gly Lys Gly Val Cys Arg Ala Gln Thr
        290                 295                 300

atg gcc aat agt gga att aaa taagtgctct gtaactgaaa gacattggcg       1023
Met Ala Asn Ser Gly Ile Lys
    305                 310

aaaacttaat aacaataaag agaagtgtgt ttatcactta catataaaaa aaaaaaaaaa  1083

aaa                                                                1086


<210> SEQ ID NO 3
<211> LENGTH: 310
<212> TYPE: PRT
<213> ORGANISM: Mus musculus

<400> SEQUENCE: 3

Met Ala Thr Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ala Leu Leu
            20                  25                  30

Lys Glu Lys Ala Ile Leu Gln Ala Thr Met Arg Glu Glu Lys Lys Leu
        35                  40                  45

Arg Val Glu Asn Ala Lys Leu Lys Lys Glu Ile Glu Glu Leu Lys Gln
    50                  55                  60
```

```
Glu Leu Ile Leu Ala Glu Ile His Asn Gly Val Glu Gln Val Arg Val
65                  70                  75                  80

Arg Leu Ser Thr Pro Leu Gln Thr Asn Cys Thr Ala Ser Glu Ser Val
                85                  90                  95

Val Gln Ser Pro Ser Val Ala Thr Thr Ala Ser Pro Ala Thr Lys Glu
            100                 105                 110

Gln Ile Lys Ala Gly Glu Glu Lys Lys Val Lys Glu Lys Thr Glu Lys
        115                 120                 125

Lys Gly Glu Lys Lys Glu Lys Gln Gln Ser Ala Ala Ala Ser Thr Asp
    130                 135                 140

Ser Lys Pro Ile Asp Ala Ser Arg Leu Asp Leu Arg Ile Gly Cys Ile
145                 150                 155                 160

Val Thr Ala Lys Lys His Pro Asp Ala Asp Ser Leu Tyr Val Glu Glu
                165                 170                 175

Val Asp Val Gly Glu Ala Ala Pro Arg Thr Val Val Ser Gly Leu Val
            180                 185                 190

Asn His Val Pro Leu Glu Gln Met Gln Asn Arg Met Val Val Leu Leu
        195                 200                 205

Cys Asn Leu Lys Pro Ala Lys Met Arg Gly Val Leu Ser Gln Ala Met
    210                 215                 220

Val Met Cys Ala Ser Ser Pro Glu Lys Val Glu Ile Leu Ala Pro Pro
225                 230                 235                 240

Asn Gly Ser Val Pro Gly Asp Arg Ile Thr Phe Asp Ala Phe Pro Gly
                245                 250                 255

Glu Pro Asp Lys Glu Leu Asn Pro Lys Lys Lys Ile Trp Glu Gln Ile
            260                 265                 270

Gln Pro Asp Leu His Thr Asn Ala Glu Cys Val Ala Thr Tyr Lys Gly
        275                 280                 285

Ala Pro Phe Glu Val Lys Gly Lys Gly Val Cys Arg Ala Gln Thr Met
    290                 295                 300

Ala Asn Ser Gly Ile Lys
305                 310


<210> SEQ ID NO 4
<211> LENGTH: 312
<212> TYPE: PRT
<213> ORGANISM: Homo sapiens

<400> SEQUENCE: 4

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
```

-continued 115 120 125

Lys Lys Gly Glu Lys Lys Glu Lys Lys Gln Gln Ser Ile Ala Gly Ser
130 135 140

Ala Asp Ser Lys Pro Ile Asp Val Ser Arg Leu Asp Leu Arg Ile Gly
145 150 155 160

Cys Ile Ile Thr Ala Arg Lys His Pro Asp Ala Asp Ser Leu Tyr Val
165 170 175

Glu Glu Val Asp Val Gly Glu Ile Ala Pro Arg Thr Val Val Ser Gly
180 185 190

Leu Val Asn His Val Pro Leu Glu Gln Met Gln Asn Arg Met Val Ile
195 200 205

Leu Leu Cys Asn Leu Lys Pro Ala Lys Met Arg Gly Val Leu Ser Gln
210 215 220

Ala Met Val Met Cys Ala Ser Ser Pro Glu Lys Ile Glu Ile Leu Ala
225 230 235 240

Pro Pro Asn Gly Ser Val Pro Gly Asp Arg Ile Thr Phe Asp Ala Phe
245 250 255

Pro Gly Glu Pro Asp Lys Glu Leu Asn Pro Lys Lys Lys Ile Trp Glu
260 265 270

Gln Ile Gln Pro Asp Leu His Thr Asn Asp Glu Cys Val Ala Thr Tyr
275 280 285

Lys Gly Val Pro Phe Glu Val Lys Gly Lys Gly Val Cys Arg Ala Gln
290 295 300

Thr Met Ser Asn Ser Gly Ile Lys
305 310

<210> SEQ ID NO 5
<211> LENGTH: 166
<212> TYPE: PRT
<213> ORGANISM: Homo sapiens

<400> SEQUENCE: 5

Ser Lys Pro Ile Asp Val Ser Arg Leu Asp Leu Arg Ile Gly Cys Ile
1 5 10 15

Ile Thr Ala Arg Lys His Pro Asp Ala Asp Ser Leu Tyr Val Glu Glu
20 25 30

Val Asp Val Gly Glu Ile Ala Pro Arg Thr Val Val Ser Gly Leu Val
35 40 45

Asn His Val Pro Leu Glu Gln Met Gln Asn Arg Met Val Ile Leu Leu
50 55 60

Cys Asn Leu Lys Pro Ala Lys Met Arg Gly Val Leu Ser Gln Ala Met
65 70 75 80

Val Met Cys Ala Ser Ser Pro Glu Lys Ile Glu Ile Leu Ala Pro Pro
85 90 95

Asn Gly Ser Val Pro Gly Asp Arg Ile Thr Phe Asp Ala Phe Pro Gly
100 105 110

Glu Pro Asp Lys Glu Leu Asn Pro Lys Lys Lys Ile Trp Glu Gln Ile
115 120 125

Gln Pro Asp Leu His Thr Asn Asp Glu Cys Val Ala Thr Tyr Lys Gly
130 135 140

Val Pro Phe Glu Val Lys Gly Lys Gly Val Cys Arg Ala Gln Thr Met
145 150 155 160

Ser Asn Ser Gly Ile Lys
165

-continued

```
<210> SEQ ID NO 6
<211> LENGTH: 13
<212> TYPE: PRT
<213> ORGANISM: Artificial
<220> FEATURE:
<223> OTHER INFORMATION: Synthetic polypeptide

<400> SEQUENCE: 6

Asp Ala Phe Pro Gly Glu Pro Asp Lys Glu Leu Asn Pro
1               5                   10
```